United States Patent [19]

Christensen et al.

[11] Patent Number: Plant 6,812

[45] Date of Patent: May 23, 1989

[54] HYBRID TEA ROSE CV. AROPOIZ

[75] Inventors: Jack E. Christensen, Ontario; Thomas F. Carruth, Canoga Park, both of Calif.

[73] Assignee: Bear Creek Gardens, Inc., Medford, Oreg.

[21] Appl. No.: 117,662

[22] Filed: Nov. 5, 1987

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Majestic, Parsons, Siebert & Hsue

[57] ABSTRACT

This invention relates to a new and distinct variety of hybrid tea rose plant cv. Aropoiz, particularly suited for cut flowers and garden decoration, identified by its lovely uniform and rich lavender color and flowers borne in clusters on long stems.

1 Drawing Sheet

The present invention relates to a new and distinct variety (cv. Aropoiz) of rose plant of the hybrid tea class. The plant is a hardy, greenhouse seedling of the tall bush type, with average to long length stems, bearing lavender colored flowers, cultivated for cut flowers and garden decoration. It was first originated by Thomas F. Carruth and Jack E. Christensen in Ontario, Calif., U.S.A. under conditions of careful control and observation, and has as its seed parent the hybrid tea rose, Lagerfeld (unpatented) and as its pollen parent, the hybrid tea rose Korblue (U.S. Plant Pat. No. 3,846).

The new rose cv. Aropoiz is particularly distinguishable from other commercialized rose cultivars by the following combination of characteristics: its tall and bushy growing habit and medium caliper stems which bear many well-shaped, large and fragrant lavender color flowers, substantially as described and illustrated herein.

As compared with the hybrid tea rose cv. Sterling Silver (U.S. Plant Pat. No. 1,433), Aropoiz has a darker petal color, is more vigorous and more productive.

Aropoiz holds its distinguishing characteristics through succeeding propagations by cuttings budding and in vitro propagation by shoot tip culture.

The new variety cv. Aropoiz may be distinguished from its seed parent, Lagerfeld, by the following combination of characteristics: Lagerfeld has relatively small leaflets, whereas Aropoiz has larger than average leaflets. Whereas the growth rate and vigor of Lagerfeld is very good for the class, the growth rate and vigor of Aropoiz is greater. The peduncle length of Aropoiz is average for the class whereas the peduncle length of Lagerfeld is very long.

The new variety cv. Aropoiz may be distinguished from its seed parent, Lagerfeld, by the following combination of characteristics: Flowers of Aropoiz have fewer petals than do flowers of Lagerfeld. The buds of Lagerfeld are smaller than the buds of Aropoiz. Flowers of Aropoiz are deeper in color than are flowers of Lagerfeld.

The accompanying drawing illustrates the new variety in color as grown in Somis, Calif., and shows the flowering thereof from bud to full bloom.

The descriptive matter which follows pertains to roses of the new variety grown in the greenhouse in Somis, Calif., and is believed generally to apply to plants grown under similar conditions of soil and climate elsewhere. Plants and flowers of the new variety grown in other locations may vary in slight detail according to the climatic, soil and cultural conditions under which the variety is grown.

Throughout this specification, color names beginning with a small letter signify that the name of that color, as used in common speech, is aptly descriptive. Color names beginning with a capital letter designate values based upon the R.H.S. Colour Chart of The Royal Horticultural Society of London, England.

FLOWER

The new variety usually bears its flowers sometimes singly, usually two to three to a stem. Flowers are borne in clusters on long length stems that are of average strength for the class. In the greenhouse and outdoors, the plant blooms abundantly and continuously during the growing season. Blooms have a strong citrus fragrance.

BUD

The peduncle is of average length for the class, of average caliper, and strong. The peduncle is moderately smooth with some stipitate glands. Bud color is near Green 143C.

Before the calyx breaks, the bud is medium in size for the class, of medium length to long, ovoid in form with a conspicuous neck. There are many foliaceous appendages and stipitate glands on the surface of the bud, with deeply serrate foliaceous parts extending beyond the tip of the bud equal to three quarters or more of its length.

As the calyx breaks, bud color is near Green 144B with a reddish tinge near the margins of the sepals of near Greyed-Purple 184A.

The inner surface of the sepals bears a fine wooly tomentum. Sepal margins are lined with stipitate glands and hairs.

As the first petal opens, buds are average in size for the class, of medium length to long and pointed in shape. The color of the outside and inside of the bud petals is between Red-Purple 72C and Red-Purple 74C.

The bud opens well and is not retarded or prevented from opening by hot, wet or dry weather.

BLOOM

The size of the bloom when fully open is large for the class, about 3 inches to about 4 inches in diameter. Petalage is very double, averaging from about 28 to 32 regularly arranged petals, plus 2 or 3 petaloids. Blooms are somewhat and full in form, with somewhat cupped petals. Petal edges are somewhat reflexed to rolled outward. When fully open, the bloom is somewhat cupped. Petals are loosely cupped and the petal edges are slightly reflexed to rolled outward.

The petals are of moderately heavy substance, of medium thickness, slightly shiny on the inside surface and slightly satiny on the outside surface. Outside petals are broadly obovate in shape with flat to rounded apices and usually bear zero to two notches. Intermediate petals are broadly obovate, sometimes scalloped, with rounded apices and usually bear zero to one notch. Inside petals are broadly obovate with rounded apices and usually bear zero to one notch.

The following paragraph describes the color values observed in a newly opened flower from a plant of the new variety grown in a greenhouse in Somis, Calif. in June of 1987.

The outside surface of the outside and inside petals is near Red-Purple 70C in color. The outside surface of the intermediate petals is near Red-Purple 74D in color.

The inside surface of the outside and intermediate petals is near Red-Purple 74C in color. The inside surface of the inside petals is near Red-Purple 70B in color.

The general color effect of the newly opened flowers is a lovely uniform and rich lavender, near Red-Purple 70C in color. Flowers open for three days are uniformly deeper in color, near Red-Purple 75A.

The following paragraph describes the color values observed in a flower open for three days indoors from a plant of the new variety in September, 1987 at Somis, Calif.

The color of the outside and inside surface of both the outside and inside petals is near Red-Purple 75A.

Petals usually drop off cleanly and are not particularly affected by cold, wet or dry weather.

Flowers grown in the month of June last from 4 to 5 or more days on the bush in the garden. Cut flowers from rose plants grown outdoors last 5 to 6 days in June when kept at living room temperatures. Cut flowers from rose plants grown in the greenhouse last from 6 to 7 days in June when kept at living room temperatures.

REPRODUCTIVE ORGANS

The many stamens are arranged regularly about the pistils; a few may also be mixed with petaloids. Filaments are short to medium in length and most have medium sized to large anthers. Anthers open approximately all at once. Mature anthers are Yellow-Orange 20A in color; immature anthers are Yellow-Orange 19A in color. Pollen is produced in moderate to abundant quantities and is Yellow-Orange 20A in color.

Pistils are average in number for the class (about 30). Styles are of average caliper, uneven, average to long in length and bunched. Stigma color is near Yellow-Orange 19C. Some ovaries are enclosed in the calyx and some protrude therefrom.

Hips of the variety are of average length and oblong in form with a conspicuous neck. They are moderately smooth with thick, dry fleshy walls. Hips are near Red 42B in color.

Sepals are permanent and of medium length. The inside surface of the sepals is near Greyed-Green 192C in color; the color of the outside sepal surface is near Greyed-Brown 199C.

Seeds are produced in few to average quantities, around 9 to 12 in number.

FOLIAGE

The compound leaves are borne in average quantities, and usually comprise 5 to 7 leaflets. They are moderately heavy and semi-glossy. Leaflets are oval in shape; their bases are usually obtuse and margins are irregularly serrate.

The color of the upper leaf surface is near Green 147A; the lower leaf surface is near Greyed-Green 191A in color. New growth is near Green 146B in color, overlaid with a tinge of near Greyed-Red 186B on the upper leaf surface. The under surface of young leaves is near Green 174A overlaid with a tinge of near Greyed-Red 186B.

The rachis is average to heavy in size. Its upper side is grooved with some stipitate glands on the edges. The underside is moderately smooth, prickly, and bears stipitate glands.

Stipules are short in length for the class, moderately narrow, and have short points which usually turn out at an angle of more than about 45°, slightly recurved toward the stem.

Plants of the new variety are, on the average, more resistant to mildew and blackspot than other cultivars now in commerce when grown under comparable conditions at Somis, Calif.

GROWTH

Plants of the new variety are of a tall, upright and bushy habit, and much branched. Plant growth is moderately vigorous. Canes are of average to heavy caliper for the class. The main stems are near Green 138A in color. They bear several large thorns which are of medium length for the class and almost straight to hooked slightly downward. Thorns are Greyed-Orange 164A in color. The thorn base is of medium length and narrow. There are several small prickles and no hairs. Small prickles are near Greyed-Yellow 161B in color.

Branches are near Greyed-Green 191A in color; they bear several large thorns of medium length and these are almost straight to hooked slightly downward. The thorn base is short and narrow. Thorns are near Greyed-Orange 160A in color. There are several small prickles near Greyed-Orange 175B and no hairs.

New shoots are near Greyed-Purple 185C in color. New shoots bear several large thorns of average length for the class. Large thorns are hooked slightly downward with moderately narrow bases of average length. Thorns are near Greyed-Purple 184B in color. There are no small prickles and no hairs.

I claim:

1. A new and distinct variety of hybrid tea rose plant cv. Aropoiz, the parts thereof, being particularly characterized by its tall and bushy growing habit; and its medium caliper stems which bear many well-shaped, large and fragrant lavender color flowers, substantially as described and illustrated herein.

* * * * *

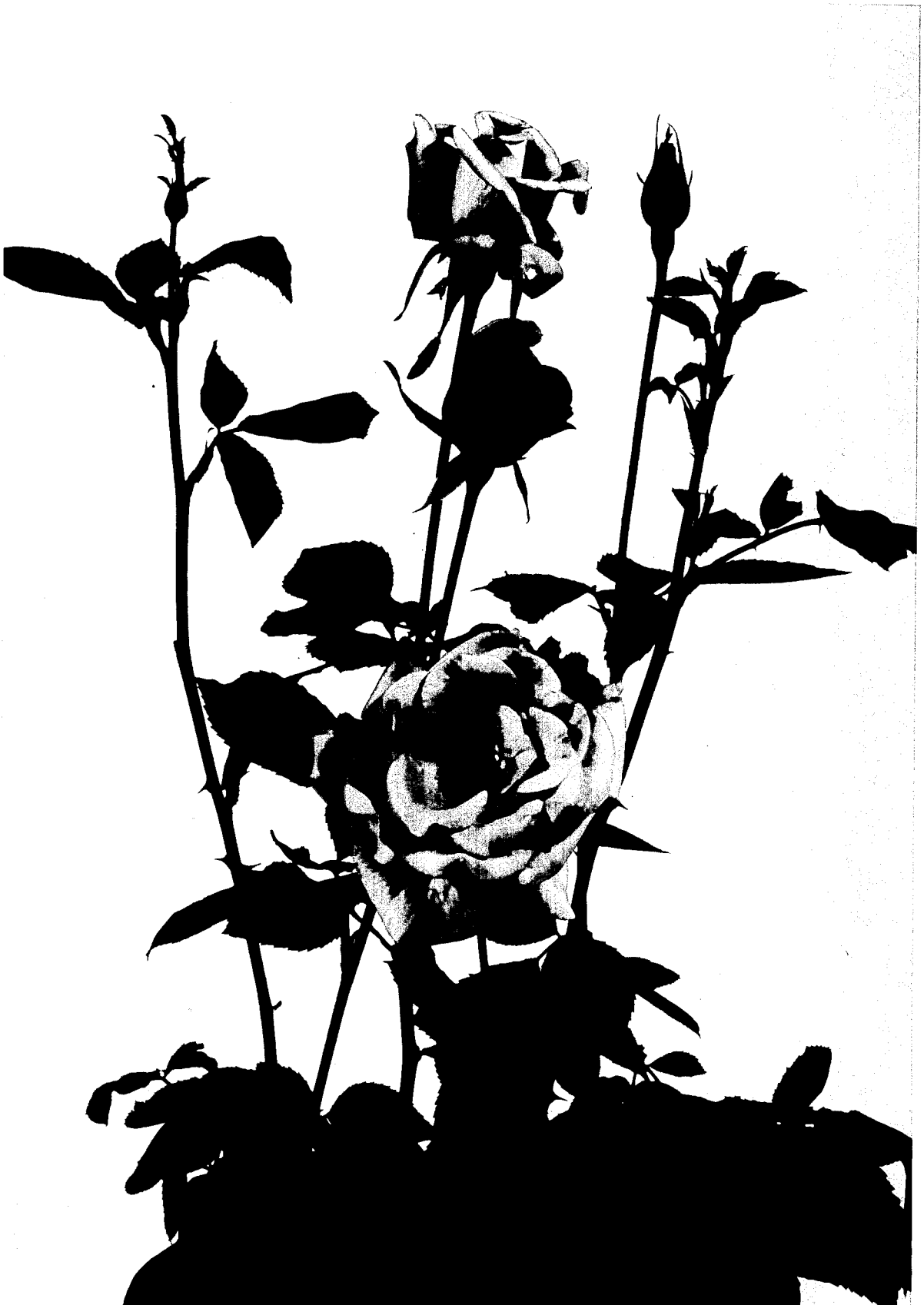

UNITED STATES PATENT AND TRADEMARK OFFICE

CERTIFICATE OF CORRECTION

PATENT NO. : Plant 6,812

DATED : May 23, 1989

INVENTOR(S) : Christensen, et al.

It is certified that error appears in the above-identified patent and that said Letters Patent is hereby corrected as shown below:

Col. 1, line 23: insert --,-- between "cuttings" and "budding";

lines 25-33: delete entire paragraph;

line 40: insert new paragraph:

-- The new variety may be distinguished from its pollen parent, Korblue, by the following combination of characteristics: Whereas the growth habit of Korblue is average height, upright and very heavily branched, the growth habit of Aropoiz is tall, bushy, and much branched. Whereas the petal color of Korblue is lavender, it is darker with more red color than the petal color of Aropoiz.--

Col. 2, line 48: delete "very" before "double".

Signed and Sealed this

Twenty-first Day of November, 1989

*Attest:*

JEFFREY M. SAMUELS

*Attesting Officer* *Acting Commissioner of Patents and Trademarks*